United States Patent
Shah et al.

(10) Patent No.: US 6,365,708 B1
(45) Date of Patent: Apr. 2, 2002

(54) POLYAMINES AND COATING COMPOSITIONS WITH ENHANCED RESISTANCE TO YELLOWING

(75) Inventors: Shailesh Shah, Dresher; Anbazhagan Natesh, North Wales; Joseph Mulvey, Lansdale; Ronald C. LaFreeda, Plymouth Meeting; Gaetano D. DeAngelis, Alburtis; Ronald T. Cash, Jr., North Wales, all of PA (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/467,585

(22) Filed: Dec. 20, 1999

(Under 37 CFR 1.47)

Related U.S. Application Data

(60) Provisional application No. 60/116,377, filed on Jan. 19, 1999.

(51) Int. Cl.[7] .................. C08G 59/10; B32B 27/38; C07C 213/04
(52) U.S. Cl. .................. 528/407; 528/103; 528/111; 528/120; 528/121; 528/122; 528/123; 564/336; 564/372; 564/453; 564/455; 564/475; 564/476; 525/504; 106/287.22; 428/413
(58) Field of Search .................. 528/103, 111, 528/120, 121, 122, 123, 407; 525/504; 564/336, 372, 453, 455, 475, 476; 106/287.22; 428/413

(56) References Cited

U.S. PATENT DOCUMENTS

| | | | |
|---|---|---|---|
| 3,903,031 A | * | 9/1975 | Matsuda et al. |
| 4,426,425 A | * | 1/1984 | Good et al. .................. 428/414 |
| 4,429,158 A | | 1/1984 | Good et al. |
| 4,525,571 A | | 6/1985 | Burba et al. |
| 4,541,958 A | | 9/1985 | Miyamoto et al. |
| 4,605,765 A | | 8/1986 | Miyamoto et al. |
| 5,346,975 A | | 9/1994 | Aoshima et al. |
| 5,934,011 A | | 8/1999 | Ishioka et al. |
| 5,994,464 A | | 11/1999 | Ohsawa et al. |

FOREIGN PATENT DOCUMENTS

| | | |
|---|---|---|
| EP | 0135330 A2 * | 3/1985 |
| GB | 1 578 303 | 11/1980 |
| JP | 61012723 A * | 1/1986 |

OTHER PUBLICATIONS

English Abstract of JP–6102723A, Jan. 1986, Japan, Horie et al.*

* cited by examiner

Primary Examiner—Robert Dawson
Assistant Examiner—Jeffrey B. Robertson
(74) Attorney, Agent, or Firm—John E. Drach; Henry E. Millison, Jr.

(57) ABSTRACT

This invention relates to novel polyamines which are the reaction product of

A) at least one nonaromatic diamine containing from 2 to 40 carbon atoms, wherein the amine groups are primary amine groups; and B) at least one epihalohydrin of the formula (II)

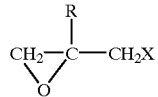

where R is hydrogen or methyl and X is chlorine or bromine; and the coatings resulting from the reaction between the above reaction product and nonaromatic epoxy resins.

11 Claims, No Drawings

POLYAMINES AND COATING COMPOSITIONS WITH ENHANCED RESISTANCE TO YELLOWING

CROSS-REFERENCE TO RELATED APPLICATIONS

This application claims priority of provisional application Serial No. 60/116,377, filed on Jan. 19, 1999.

FIELD OF THE INVENTION

This invention relates to polyamines and to compositions produced by the reaction of the polyamines with epoxy resins.

BACKGROUND OF THE INVENTION

Certain aromatic polyamines are known for use as hardening agents for epoxy resins. However, coatings obtained from the reaction between these polyamines and epoxy resins, especially aromatic epoxy resins, often yellow with age, rendering them of limited usefulness.

SUMMARY OF THE INVENTION

Polyamines have now been discovered that can be reacted with nonaromatic epoxy resins, i.e. epoxy resins based on aliphatic or cycloaliphatic polyols to form coatings having a high resistance to yellowing with age and with exposure to ultraviolet radiation.

The polyamines of the invention are the reaction products of

A) at least one nonaromatic diamine containing from 2 to 40 carbon atoms, wherein the amine groups are primary amine groups; and B) at least one epihalohydrin of the formula

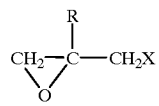

(II)

where R is hydrogen or methyl and X is chlorine or bromine; wherein the mole ratio of component A) to component B) is about 2:1.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The polyamines of the invention, which are the reaction products of components A) and B) given above, preferably have the formula

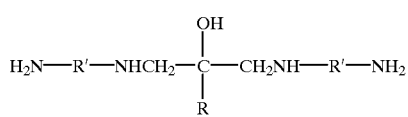

(I)

wherein R is hydrogen or methyl, and R' is a $C_{2-40}$ aliphatic, cycloaliphatic, aliphatic cycloaliphatic, or polyoxyalkylene group, wherein the first three of these groups can optionally contain one or more nonconjugated double bonds. However, other nonaromatic diamines can also be used in the practice of the invention.

Examples of the nonaromatic diamines of component A) include, but are not limited to, the following: 1,3-bis (aminomethyl)cyclohexane, ethylenediamine, diethylenetriamine, triethylenetetramine, hexamethylenediamine, 2-methyl-1,5-pentanediamine-, 1,6-hexamethylenediamine, 2-heptyl-3,4-bis(9-aminononyl)-1-pentylcyclohexane(dimeryldiamine), polyoxyalkylene diamine, e.g. polyoxypropylene diamine, isophoronediamine, norbornodiamine, 2.5(2.6)-bis (aminomethyl)bicyclo(2.2.1) heptane, 4,4'-dicyclohexylmethane diamine, 1,4-diaminocyclohexane, menthanediamine, and bis(aminomethyl)cyclohexane.

Preferred nonaromatic diamines include those based on (i.e. containing) straight or branched chain saturated aliphatic groups, and those based on at least one cycloaliphatic group, optionally containing one or more nonconjugated double bonds.

Component B) is preferably epichlorohydrin, although epibromohydrin, 2-methyl epichlorohydrin, and 2-methyl epibromohydrin can also be used as component B).

The reaction between about 2 moles (e.g. from 2 to 2.1 moles) of component A) and one mole of component B) can be carried out by slowly adding component B) to component A) under a nitrogen atmosphere at a temperature in the range of from 200 to 100° C., preferably from 23° to 60° C. with stirring. After completion of the addition, from 0.5 to 1 mole of alkali metal hydroxide, preferably sodium hydroxide (a 50% aqueous solution for example) is added slowly with stirring. After this addition the mixture is heated to a temperature in the range of 650° to 95° C. for a period of several hours. The reaction mixture is then filtered to remove insoluble salts, and the reaction product isolated from the filtrate, e.g. by the removal of volatile components therefrom using vacuum distillation.

The polyamine of formula I can then be reacted with a nonaromatic epoxy resin at ambient temperatures to produce the coatings of the invention. The nonaromatic epoxy resin is based on an aliphatic or cycloaliphatic polyol, e.g. the polyglycidyl ether of polyether polyol, cycloaliphatic diepoxides, diglycidyl ether of hydrogenated Bis-phenol A, and the like.

The polyamine of formula I can be mixed with the nonaromatic epoxy resin in various proportions to form the coatings of the invention. However, weight ratios of (0.25 to 0.60):1 (polyamine:epoxy resin) are most suitable.

The coatings of the invention are light-stable and are accordingly very useful for outdoor applications. The coatings resist yellowing even after long periods of time exposed to daylight, which of course contains significant quantities of ultraviolet light.

The invention will be exemplified but not limited by the following examples.

EXAMPLES

Example 1

349.30 grams (2.051 moles) of isophoronediamine were added to a reaction vessel at 24° C. under a nitrogen atmosphere. 92.50 grams (1.000 moles) of epichlorohydrin was then added slowly with stirring over a period of one hour, while controlling the exothermic reaction to a reaction temperature of 45–50° C. After the addition, the mixture was stirred at 52° C. for 30 minutes. Then 79.20 grams (0.990 moles) of 50% NaOH was added over a period of 30 minutes at a temperature of 43–46° C. The resulting mixture was heated to 70° C. and held at this temperature for one hour. The temperature was then raised to 90° C. and held at this temperature with stirring for an additional hour. The temperature was reduced to 70° C. and 2.70 grams (0.025 moles) of $Na_2CO_3$ were added over 5 minutes, and the mixture stirred at 70° C. for 3 hours. 513.1 grams of crude reaction product were obtained, including a salt precipitate.

The reaction mixture was filtered to give 206.0 grams of filtrate and 252.0 grams of suspended solids on the filter paper. The suspended solids were added to 200 grams of water with stirring. Two layers separated. The top oily layer was separated off and added to the filtrate to give 396.60 grams of crude reaction product, which was then vacuum stripped (30 mm, 100° C.) to remove volatile components to give a residual reaction product (285.79 grams).

Example 2

315.7 grams (2.05 moles) of 2,5(2,6)-bis(aminomethyl) bicyclo(2.2.1)heptane and 79.20 grams (0.99 moles) of 50% NaOH solution were added to a reaction flask under a nitrogen atmosphere. Then 92.50 grams (1.00 mole) of epichlorohydrin were added with stirring over a period of about 1.5 hours. During this period the temperature rose from 28° to 84° C. The mixture was then held at 84–90° C. with stirring for 2 hours. The mixture was cooled to 70° and 2.70 grams (0.025 moles) of $Na_2CO_3$ were added and held with stirring at 70° C. for 3 hours. Next, 225.0 grams of water were added and the resulting mixture cooled to 40° C. The mixture was vacuum stripped (15 mm at 105° C.) and filtered under nitrogen to give a clear filtrate reaction product (140.42 grams).

Example 3

293.71 grams (2.53 moles) of 2-methyl-1,5-pentanediamine and 98.41 (1.23 moles) of 50% NaOH were added to a reaction flask under a nitrogen atmosphere. Then 114.22 grams (1.23 mole) of epichlorohydrin were added with stirring over a period of 2 hours during which the temperature rose from 23° to 101° C. The mixture was stirred at 85–90° C. for 2.5 hours, and then cooled to 70° C. 3.33 grams (0.031 moles) of $Na_2CO_3$ were slowly added and the resulting mixture held with stirring at 65–70° C. for 3 hours. The mixture was cooled to room temperature, filtered, and the filtrate vacuum stripped (10 mm at 95° C.). The residue was filtered in a filter press to give 235.9 grams of filtrate reaction product.

Example 4

494.1 grams (2.05 moles) of polyoxypropylenediamine and 81.2 g (1.02 moles) of 50% NaOH solution were added to a reaction flask under a nitrogen atmosphere. Then 92.5 grams (1.00 mole) of epichlorohydrin were added with stirring over a period of about 1.5 hours, during which time the temperature rose from 29° C. to 108° C. The mixture was stirred for 2 hours at 91° C., and then cooled to 70° C. 2.7 grams (0.025 moles) of $Na_2CO_3$ were added and the resulting mixture held at 65–72° C. with stirring for 3 hours. The mixture was heated to 120° C. and filtered in a filter press under pressure. The distillate was vacuum stripped (20 mm at 120° C.) to give 479.0 grams of residual reaction product.

Example 5

965.5 grams (6.27 moles) of 2,5(2,6)-bis (aminomethyl) bicyclo (2.2.1) heptane and 242.8 grams (3.0 moles) of 50% NaOH solution were added to a reaction flask under a nitrogen atmosphere with stirring. Then 283.4 grams (3.06 moles) of epichlorohydrin were added with stirring over a period of about 2 hours, during which time the temperature rose from 24° C. to 91° C. The reaction mixture was maintained with stirring at 86–91° C. for 2 hours, and cooled to 70° C. Then 8.3 grams (0.078 moles) of $Na_2CO_3$ were added and the resulting mixture maintained with stirring at 65–70° C. for 3 hours. The reaction mixture was next heated to 80° C. and filtered through a filter press. The filtrate was vacuum stripped (10 mm at 150° C.) and cooled to 80° C. 849.39 grams of reaction product were obtained as the residue.

Example 6

582.5 grams (4.1 moles) of 1,3-bis(aminomethyl) cyclohexanone and 159.6 grams (1.98 moles) of 50% NaOH were added to a reaction flask under a nitrogen atmosphere. Then 185.1 grams (2.0 moles) of epichlorohydrin were added with stirring over a period of about 2.5 hours, during which time the reaction temperature was allowed to rise from 24° C. to 85° C. The reaction mixture was stirred at 90–95° C. for 2 hours, cooled to 50° C., 54 grams (0.05 moles) of $Na_2CO_3$ added, and stirred for an additional 3 hours at 65–70° C. The reaction mixture was cooled, filtered in a filter press and the filtrate vacuum stripped (20–30 mm at 100–102° C.). The hot residue (70° C.) was again filtered, resulting in 616.73 grams of filtrate reaction product.

Example 7

The following nonaromatic epoxy resin compositions and hardener compositions were mixed together at ambient temperatures, and the resulting mixtures (A–K) were coated on steel panels, allowed to harden, and tested as shown in Table 1 below:

TABLE 1

| Component | A | B | C | D | E | F | G | H | I | J | K |
|---|---|---|---|---|---|---|---|---|---|---|---|
| Nonaromatic epoxy resin compositions. Numbers represent weight ratios of ingredients. | | | | | | | | | | | |
| Epalloy ® 5000[1] | 100 | | 100 | | 100 | | 100 | | 100 | | |
| Epalloy ® RK851[2] | | 100 | | 100 | | 100 | | 100 | | 100 | 80 |
| Photomer 4399[3] | | | | | | | | | | | 10 |
| UC ERL 4206[4] | | | | | | | | | | | 10 |
| Nonaromatic polyamine hardener compositions. Numbers represent weight ratios of ingredients. | | | | | | | | | | | |
| NBDA Epi-Adduct[5] | 28 | 31 | 13.8 | 15 | 28 | 31 | 28 | 31 | 25 | 25 | 15 |
| Benzyl alcohol | | | | | 22 | 9 | | | | | |

TABLE 1-continued

| Component | A | B | C | D | E | F | G | H | I | J | K |
|---|---|---|---|---|---|---|---|---|---|---|---|
| Dowanol ® PM[6] | | | | | | | | | 28 | 31 | |
| Versamine ® EH50[7] | | | | | | | 10 | 10 | | | |
| AEEA[8] | | | 2.3 | 5 | | | | | | | 2.5 |
| AEP[9] | | | 4.6 | 5 | | | | | | | 2.5 |
| TMD[10] | | | 2.3 | | | | | | | | 5 |
| Mix Weight Ratio: | | | | | | | | | | | |
| Resin | 100 | 100 | 100 | 100 | 100 | 100 | 100 | 100 | 100 | 100 | 100 |
| Hardener | 28 | 31 | 23 | 25 | 50 | 40 | 38 | 41 | 53 | 56 | 25 |
| Vis. of Hardener (Cps. @ 25° C.) | 110,000 | 110,000 | 700 | 750 | 550 | 4,100 | 13,000 | 15,000 | 150 | 170 | 500 |
| Set to touch time (hrs.) | 3.5 | 1 | 4 | 1.5 | 3 | 1.5 | 1.5 | 0.75 | 3.5 | 1.5 | 1 |
| Tack free time (hrs.) | 5.5 | 2.25 | 8 | 2.5 | 3.5 | 2 | 3.5 | 2 | 5.5 | 2.5 | 1.5 |
| Thru cure time (hrs.) | 8 | 3 | 12 | >24 | 4.5 | 3 | 4.5 | 2.5 | 6.5 | 3.5 | 5.0 |
| Tg (° C.)[11] | 109 | 118 | | | 53 | 101 | 110 | 120 | 95 | 110 | |
| QUV Exposure[12] (D65) after 7 days: | | | | | | | | | | | |
| DL[13] (darkening) | −4.22 | −5.08 | −3.69 | −3.62 | −4.06 | −5.08 | −0.76 | −0.89 | −4.48 | −3.66 | −3.65 |
| Db[14] (yellowing) | 17.93 | 21.75 | 14.40 | 16.78 | 19.84 | 20.95 | 4.87 | 5.97 | 20.34 | 22.99 | 15.36 |
| DE[15] (overall) | 18.61 | 22.07 | 15.16 | 16.98 | 20.26 | 21.67 | 5.14 | 6.29 | 20.99 | 23.41 | 16.22 |
| Repeat QUV on force cured panels - 24 hours @ 140° F. | | | | | | | | | | | |
| DL | −3.10 | −4.03 | | | | | −0.39 | −1.92 | | | |
| Db | 17.79 | 23.24 | | | | | 4.92 | 6.67 | | | |
| DE | 18.16 | 23.70 | | | | | 5.04 | 7.05 | | | |

Notes for Table 1
[1]Diglycidyl ether of hydrogenated Bis-phenol A
[2]Predominantly the diglycidyl ether of hydrogenated Bis-phenol A
[3]Dipentaerythritol pentaacrylate
[4]Vinyl cyclohexenedioxide
[5]The reaction product produced by the process of Example 2
[6]Propylene glycol monoether from Dow Chemical Co.
[7]Tertiary amine from Henkel Corporation
[8]Aminoethyl ethanolamine from Union Carbide Corp.
[9]Aminoethyl piperazine from Dow Chemical Co.
[10]Trimethyl hexamethylenediamine from Hüls Corp.
[11]Tg is the glass transition temperature in degrees centigrade
[12]QUV Exposure is the Q Panel Ultraviolet exposure carried out according to ASTM Method G53.
[13]DL is the difference in lightness and darkness
[14]Db is the difference in yellowing
[15]DE is the difference in the overall coloring Example 8

The following epoxy resin compositions and hardener compositions were mixed together at ambient temperatures, and the resulting mixtures (A–J) were coated on steel panels, allowed to harden, and tested as shown in Table 2 below:

TABLE 2

| Component | A | B | C | D | E | F | G | H | I | J |
|---|---|---|---|---|---|---|---|---|---|---|
| Epoxy resin compositions. Numbers represent weight ratios of ingredients. | | | | | | | | | | |
| Epalloy ® 5000 | 100 | | 100 | 100 | | | 100 | | | |
| Epalloy ® RK851 | | 100 | | | 100 | | | | | |
| DER 331[16] | | | | | | | | 100 | | 100 |
| Shell DPL 700[17] | | | | | | 100 | | | | |
| Eponox ® 1510[18] | | | | | | | | | 100 | |
| Polyamine hardener compositions. Numbers represent weight ratios of ingredients. | | | | | | | | | | |
| NBDA Epi-Adduct[5] | 28 | 31 | 28 | 28 | 31 | | | | | |
| Versamine ® C-31[19] | | | | | | | 39 | | | 45 |
| Versamine ® EH-50 | 10 | 10 | 10 | 5 | 5 | | | | 10 | |
| Dowanol ® PM | 12 | 9 | | 17 | 14 | | | | | |
| Benzyl alcohol | | | 12 | | | | | | | |
| Shell DPC 750[20] | | | | | | 38 | | | | |
| NBDA Epi Adduct in PM Solvent[21] | | | | | | | | 42 | | 36 |

TABLE 2-continued

| Component | A | B | C | D | E | F | G | H | I | J |
|---|---|---|---|---|---|---|---|---|---|---|
| Mix Weight Ratio: | | | | | | | | | | |
| Resin | 100 | 100 | 100 | 100 | 100 | 100 | 100 | 100 | 100 | 100 |
| Hardener | 50 | 50 | 50 | 50 | 50 | 38 | 39 | 42 | 46 | 45 |
| Viscosity | 570 | 1100 | 1525 | 250 | 560 | | | | | |
| Gel Time | 57' | 26' | 41' | 63' | 32' | 32' | 146' | 34' | 67' | 43' |
| BK Cure (hrs.)[22]: | | | | | | | | | | |
| Set to touch | 1 | 1 | 2 | 3 | 1 | 3 | 8 | 1 | 2 | 3 |
| Tack free | 3.5 | 2 | 3¼ | 4 | 2 | 4 | 13 | 2 | 4 | 5 |
| Thru cure | 8 | 2.5 | 4.5 | 10 | 2.5 | 8 | 22 | 3 | 5 | 8 |
| Gloss Before - | | | | | | | | | | |
| 20° | 63.8 | 84.6 | 72.1 | 86.0 | 83.3 | 90.3 | 89.0 | 101.7 | 86.9 | 100.7 |
| 60° | 89.1 | 94.3 | 93.5 | 92.8 | 94.2 | 95.3 | 94.9 | 103.1 | 90.1 | 103.0 |
| QUV Exposure | | | | | | | | | | |
| (D65) after 1 week: | | | | | | | | | | |
| DL (darkening) | −2.87 | −2.10 | −3.73 | −1.60 | −2.01 | −2.43 | −2.71 | −5.96 | −3.13 | −5.29 |
| Db (yellowing) | 10.43 | 7.28 | 19.19 | 5.90 | 7.89 | 11.70 | 16.26 | 25.2 | 12.50 | 26.77 |
| DE (overall) | 11.05 | 7.95 | 19.79 | 6.45 | 8.59 | 12.08 | 16.84 | 23.96 | 13.11 | 24.36 |
| Gloss After 1 week: | | | | | | | | | | |
| 20° | 3.2 | 37.3 | 21.1 | 22.7 | 32.9 | 89.6 | 86.6 | 85.0 | 86.2 | 85.3 |
| 60° | 19.3 | 78.3 | 62.9 | 55.1 | 70.4 | 70.4 | 95.5 | 93.8 | 94.0 | 94.3 |
| QUV Exposure | | | | | | | | | | |
| (D65) after 2 weeks: | | | | | | | | | | |
| DL (darkening) | −2.58 | −2.46 | −3.71 | −2.38 | −2.78 | −3.31 | −3.64 | −7.36 | −2.73 | −6.39 |
| Db (yellowing) | 7.96 | 8.82 | 18.06 | 7.20 | 11.53 | 14.14 | 19.34 | 25.24 | 9.68 | 26.31 |
| DE (overall) | 8.67 | 9.57 | 18.69 | 7.95 | 17.31 | 14.65 | 19.97 | 26.29 | 10.39 | 27.09 |
| Gloss After 2 weeks: | | | | | | | | | | |
| 20° | 3.0 | 30.5 | 15.9 | 22.8 | 31.2 | 78.1 | 72.0 | 78.8 | 84.9 | 74.9 |
| 60° | 18.0 | 75.4 | 59.0 | 63.4 | 71.8 | 92.5 | 89.5 | 95.8 | 93.3 | 90.7 |
| QUV Exposure | | | | | | | | | | |
| (D65) after 3 weeks: | | | | | | | | | | |
| DL (darkening) | −2.39 | −2.92 | −3.79 | −2.74 | −3.48 | −3.93 | −4.24 | −8.06 | −2.46 | −7.13 |
| Db (yellowing) | 7.50 | 11.66 | 18.30 | 9.19 | 16.77 | 16.43 | 21.28 | 26.74 | 8.13 | 27.92 |
| DE (overall) | 8.24 | 12.46 | 18.96 | 9.98 | 17.51 | 17.01 | 22.09 | 27.93 | 8.86 | 28.57 |
| Gloss After 3 weeks: | | | | | | | | | | |
| 20° | 2.85 | 36.5 | 22.6 | 28.7 | 26.3 | 81.3 | 58.4 | 73.3 | 84.7 | 69.1 |
| 60° | 17.2 | 78.9 | 60.3 | 62.9 | 68.7 | 93.9 | 87.5 | 97.4 | 93.7 | 89.2 |

Notes for Table 2
[16]Bisphenol A/epichlorohydrin epoxy resin from Dow Chemical Co.
[17]A blend of hydrogenated Bisphenol A/epichlorohydrin based epoxy resin with a multifunctional acrylate monomer from Shell Chemical Co.
[18]Hydrogenated Bisphenol A - epichlorohydrin epoxy resin from Shell Development Corp.
[19]A modified cycloaliphatic amine from Henkel Corporation.
[20]A cycloaliphatic amine from Shell Development Corp.
[21]The reaction product obtained from the process of Example 5 diluted in a mixture of propylene glycol monomethyl ether from Dow Chemical Co.
[22]BK Cure is measured by coating a 1" × 12" glass strip with the epoxy resin composition and immediately attaching a timer with a prong in contact with the bottom of the glass strip, wherein the timer moves up the strip at a rate of 2" per hour. When the prong no longer scratches the coating, the length of the scratched surface is measured, which gives the time required for the coating to cure.

What is claimed is:

1. A reaction product comprising

A) at least one polyamine of formula I

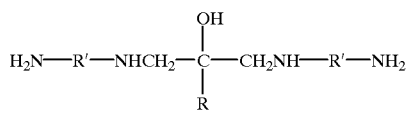

(I)

wherein R is hydrogen or methyl, and R' is a $C_{2-40}$ aliphatic, cycloaliphatic, aliphatic cycloaliphatic, or polyoxyalkylene group, wherein the first three of these groups can optionally contain one or more nonconjugated double bonds; and B) at least one epichlorohydrin of the formula

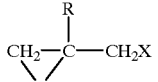

(II)

where R is hydrogen or methyl and X is chlorine or bromine; and wherein the mole ratio of component A) to component B) is about 2:1.

2. The reaction product of claim 1 wherein component B) is epichlorohydrin.

3. The reaction product of claim 1 wherein the reaction between components A) and B) is carried out in the presence of an alkali metal hydroxide.

4. A coating composition comprising

I) the reaction product of claim 1; and

II) a nonaromatic epoxy resin.

5. The coating resulting from the coating composition of claim 4.

6. The reaction product of claim 1 wherein R' is an aliphatic group optionally containing one or more nonconjugated double bonds.

7. The reaction product of claim 1 wherein R' is a cycloaliphatic group optionally containing one or more nonconjugated double bonds.

8. The reaction product of claim 1 wherein R' is an aliphatic cycloaliphatic group optionally containing one or more nonconjugated double bonds.

9. The reaction product of claim 1 wherein R' is a polyoxyalkylene group.

10. The coating composition of claim 4 wherein component II is based on an aliphatic or cycloaliphatic polyol.

11. The coating composition of claim 4 wherein the weight ratio of component A) to component B) is about (0.25 to 0.60):1.

* * * * *